United States Patent
Niwa et al.

(10) Patent No.: US 10,624,528 B2
(45) Date of Patent: Apr. 21, 2020

(54) CONNECTOR

(71) Applicant: OLYMPUS CORPORATION, Tokyo (JP)

(72) Inventors: Hiroshi Niwa, Koganei (JP); Minoru Sato, Hino (JP); Koji Omori, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 373 days.

(21) Appl. No.: 15/485,463

(22) Filed: Apr. 12, 2017

(65) Prior Publication Data

US 2017/0215702 A1    Aug. 3, 2017

Related U.S. Application Data

(63) Continuation of application No. PCT/JP2016/061814, filed on Apr. 12, 2016.

(30) Foreign Application Priority Data

Jun. 3, 2015 (JP) .................................. 2015-113344

(51) Int. Cl.
*A61B 1/00* (2006.01)
*A61B 1/06* (2006.01)
(Continued)

(52) U.S. Cl.
CPC ...... *A61B 1/00124* (2013.01); *A61B 1/00018* (2013.01); *A61B 1/0051* (2013.01);
(Continued)

(58) Field of Classification Search
CPC combination set(s) only.
See application file for complete search history.

(56) References Cited

U.S. PATENT DOCUMENTS 4,404,964 A * 9/1983 Kambara .......... A61B 1/00124
396/17
5,469,841 A * 11/1995 Kobayashi ........ A61B 1/00124
600/158

(Continued)

FOREIGN PATENT DOCUMENTS

CN    101518436 A    9/2009
CN    102573607 A    7/2012
(Continued)

OTHER PUBLICATIONS

International Search Report dated Jul. 12, 2016 issued in PCT/JP2016/061814.

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

An endoscope connector includes: a fitting portion that has a cylindrical shape, and electrically connects an endoscope for observation of a subject to an external apparatus, the external apparatus processing information of the observed subject; a planar part provided on at least a portion of the cylindrical shape of the fitting portion; and an electroconductive part that is provided to be electrically conductive on the planar part and performs communication with the external apparatus.

7 Claims, 6 Drawing Sheets

(51) Int. Cl.
  *G02B 23/26*  (2006.01)
  *A61B 1/005*  (2006.01)
  *A61B 1/05*   (2006.01)

(52) U.S. Cl.
  CPC .................. *A61B 1/05* (2013.01); *A61B 1/06* (2013.01); *G02B 23/26* (2013.01)

(56) References Cited

U.S. PATENT DOCUMENTS

| | | | |
|---|---|---|---|
| 5,810,620 A | 9/1998 | Kobayashi et al. | |
| 5,865,726 A * | 2/1999 | Katsurada | A61B 1/0008 600/121 |
| 6,043,839 A * | 3/2000 | Adair | A61B 1/00135 257/E25.032 |
| 6,211,904 B1 * | 4/2001 | Adair | A61B 1/00082 257/E25.032 |
| 9,833,127 B2 * | 12/2017 | Tomatsu | A61B 1/00124 |
| 2002/0080248 A1 * | 6/2002 | Adair | A61B 1/00096 348/230.1 |
| 2002/0098732 A1 | 7/2002 | Shimizu | |
| 2005/0177027 A1 * | 8/2005 | Hirata | A61B 1/0676 600/179 |
| 2007/0106119 A1 * | 5/2007 | Hirata | A61B 1/00096 600/179 |
| 2009/0216086 A1 | 8/2009 | Omori | |
| 2012/0202385 A1 * | 8/2012 | Miyagi | A61B 1/00124 439/626 |
| 2013/0035550 A1 * | 2/2013 | Watanabe | G02B 6/4298 600/132 |
| 2014/0213850 A1 * | 7/2014 | Levy | A61B 1/00137 600/156 |

FOREIGN PATENT DOCUMENTS

| | | | | |
|---|---|---|---|---|
| JP | 64002622 A * | 1/1989 | | A01B 1/05 |
| JP | H06-250103 A | 9/1994 | | |
| JP | H06-251829 A | 9/1994 | | |
| JP | H07-184857 A | 7/1995 | | |
| WO | WO 2011052408 A1 | 5/2011 | | |

* cited by examiner

CONNECTOR

CROSS REFERENCE TO RELATED APPLICATION

This application is a continuation application of PCT/JP2016/061814 filed on Apr. 12, 2016 and claims benefit of Japanese Application No. 2015-113344 filed in Japan on Jun. 3, 2015, the entire contents of which are incorporated herein by this reference.

BACKGROUND OF THE INVENTION

1. Field of the Invention

The present invention relates to an endoscope connector suitable for high-speed transmission.

2. Description of the Related Art

In a medical field, an endoscope that allows for observation of organs and the like in a body cavity through insertion of an elongated insertion section into the body cavity has been widely used in the past. To display an observation image of the organs and the like in the body cavity on a monitor, an electronic endoscope in which a solid-state image pickup device such as a charge coupled device (CCD) is disposed in an image pickup section at a distal end or a rear end of the insertion section of the endoscope, an optical endoscope that allows for naked-eye observation and includes an external camera at an eyepiece section, and the like are used.

A signal outputted from the image pickup device provided in the electronic endoscope or the external camera is converted into a video signal by an image processor that is separated from the electric endoscope, the external camera, and the like, and the video signal is outputted to the monitor. The image processor is connected, through an endoscope connector, to the electronic endoscope, the external camera, and the like that are separately configured. In addition, various kinds of treatment instruments used in medical treatment or an operation are also connected, through the endoscope connector, to a control apparatus serving as a supply source of energy.

Examples of such an endoscope connector include an endoscope connector disclosed in International Publication No. WO2011-52408. Incidentally, the endoscope connector adopted to the endoscope is often formed in a cylindrical shape in consideration of handling property. In addition, a contact portion (a fitting portion) between the endoscope connector and a receptacle of the external apparatus may preferably have a cylindrical shape that is coincident with an exterior shape of the endoscope connector, namely, the cylindrical shape, in terms of water-tightness. As a result, electric contacts are provided on a front surface or a side surface of the cylindrical fitting portion in the endoscope connector. When the electric contacts are provided on the front surface of the fitting portion, the electric contacts are simply brought into contact with electric contact of the receptacle, thereby performing electrical conduction. In contrast, when the electric contacts are provided on the side surface of the fitting portion, the electric contacts of the endoscope connector are brought into contact with the electric contacts of the receptacle while rubbing against each other in fitting. Therefore, stains of the electric contacts are removed in sliding, which allows for favorable electric connection. The device disclosed in International Publication No. WO2011-52408 includes the electric contacts provided on a circumferential surface of the cylindrical shape of the fitting portion, and has easiness of gripping, a water-tight structure, and characteristics excellent in electric connection.

Incidentally, in recent years, resolution of an image transmitted by the endoscope has been increased, and a data communication speed required for the endoscope connector has also been increased. To dispose a circuit device necessary for such high-speed transmission, it is necessary to increase a size of the circuit substrate provided in the endoscope connector. It is not possible to dispose the circuit substrate such that the substrate surface becomes parallel to a radial direction of the endoscope connector, because of limitation of outer size of the endoscope connector, and the circuit substrate is accordingly disposed in a longitudinal direction of the endoscope connector. Therefore, it is not possible to bring terminals on the circuit substrate (hereinafter, referred to as substrate terminals) into direct contact with electric contacts of the endoscope connector (hereinafter, referred to as connector contacts), and it is necessary to connect the substrate terminals to the connector contacts through wirings. Alternatively, a method in which the connector contacts are directly connected to terminals of an intermediate substrate, a substrate surface of which is disposed parallel to the radial direction of the endoscope connector, and the intermediate substrate is connected to the substrate terminals through wiring is adopted.

SUMMARY OF THE INVENTION

An endoscope connector according to an aspect of the present invention includes: a fitting portion that has a cylindrical shape, and electrically connects an endoscope for observation of a subject to an external apparatus, the external apparatus processing information of the observed subject; a planar part provided on at least a portion of the cylindrical shape of the fitting portion; and an electroconductive part that is provided to be electrically conductive on the planar part and performs communication with the external apparatus.

DETAILED DESCRIPTION OF THE PREFERRED EMBODIMENT(S)

An embodiment of the present invention is described in detail below with reference to drawings.

Figure 1:
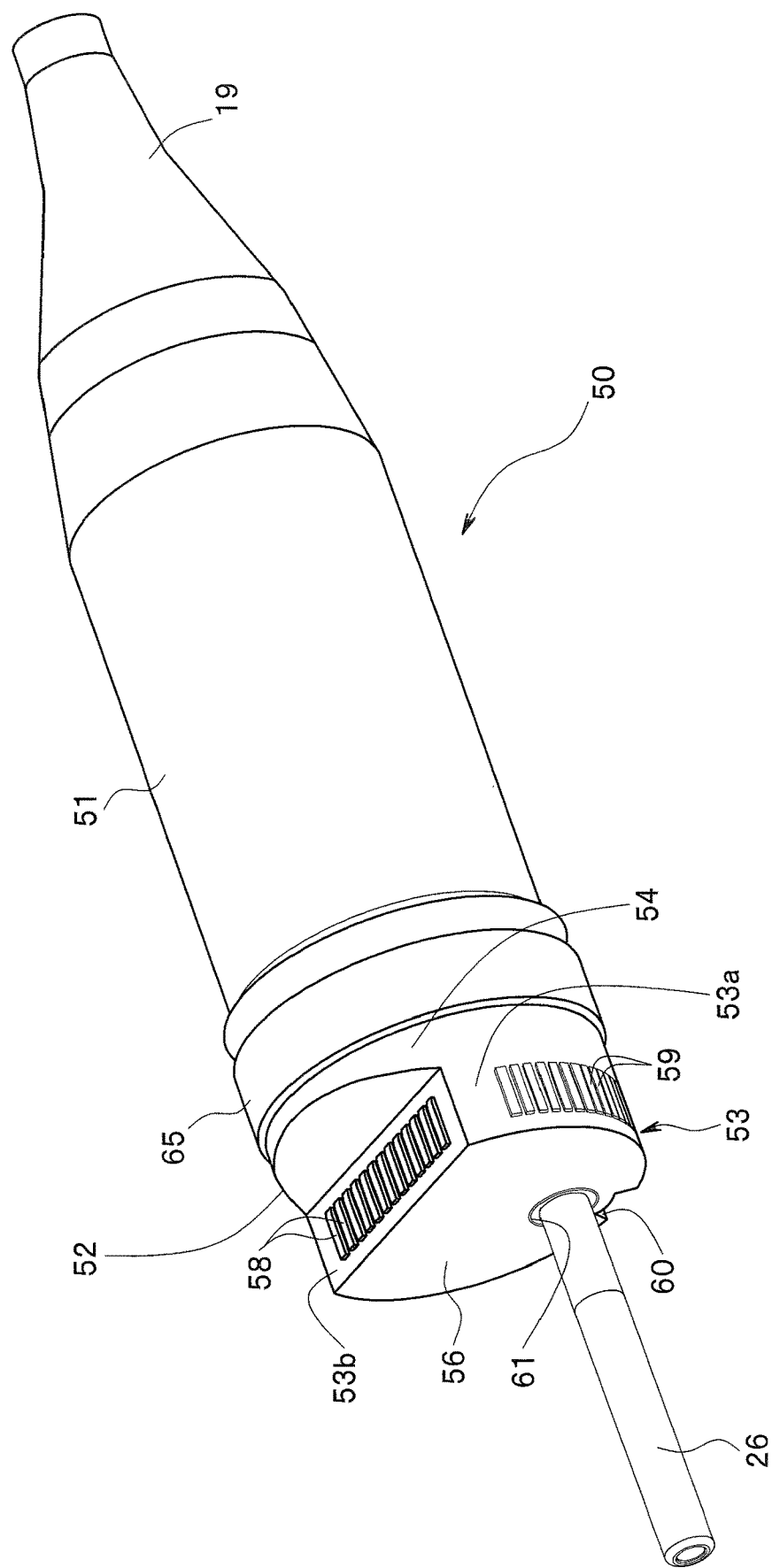
FIG. 1 is a perspective view illustrating an endoscope connector according to a first embodiment of the present invention.
Figure 2:
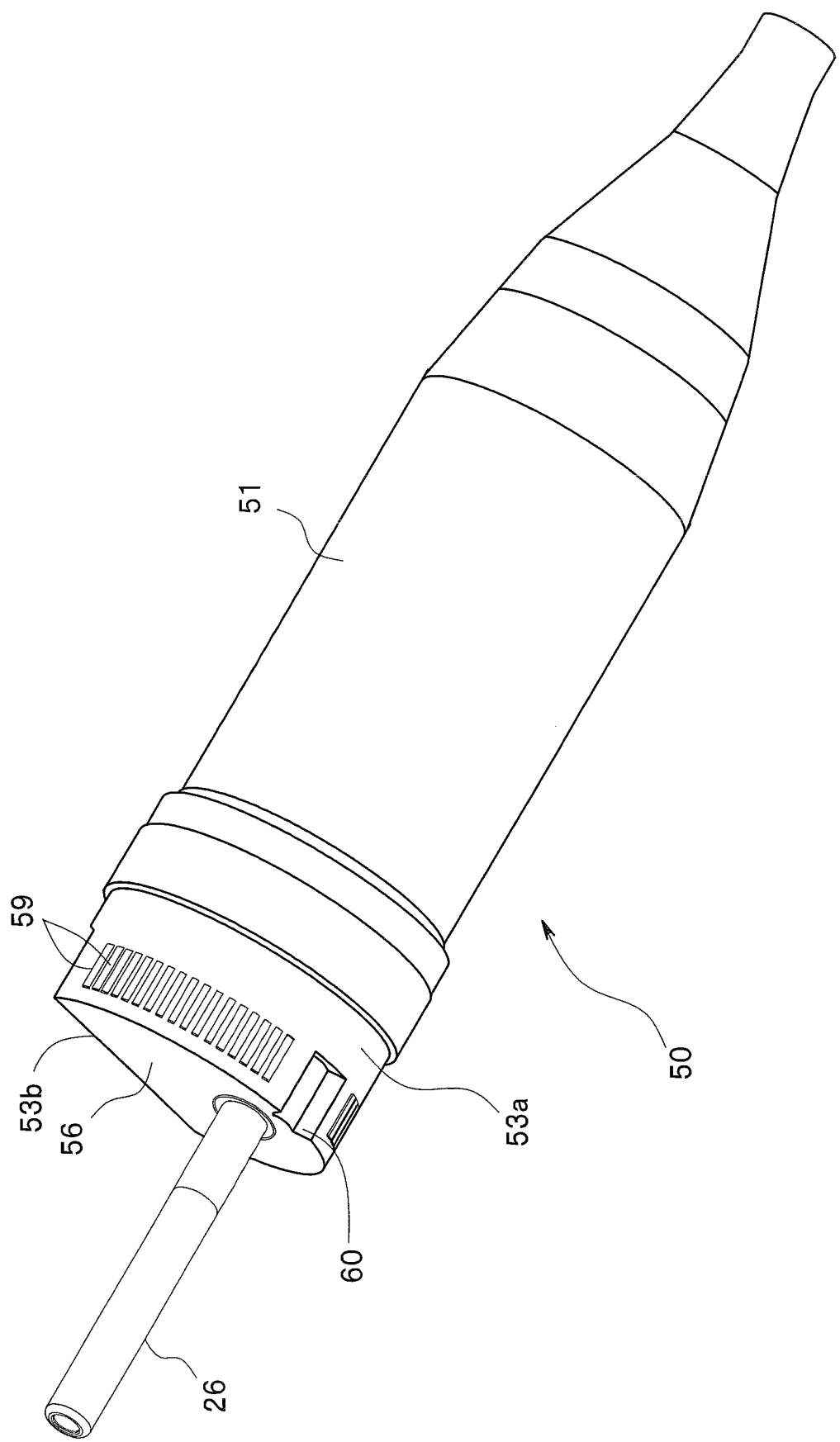
FIG. 2 is a perspective view illustrating a configuration of the endoscope connector as viewed from an angle different from an angle of FIG. 1.
Figure 3:
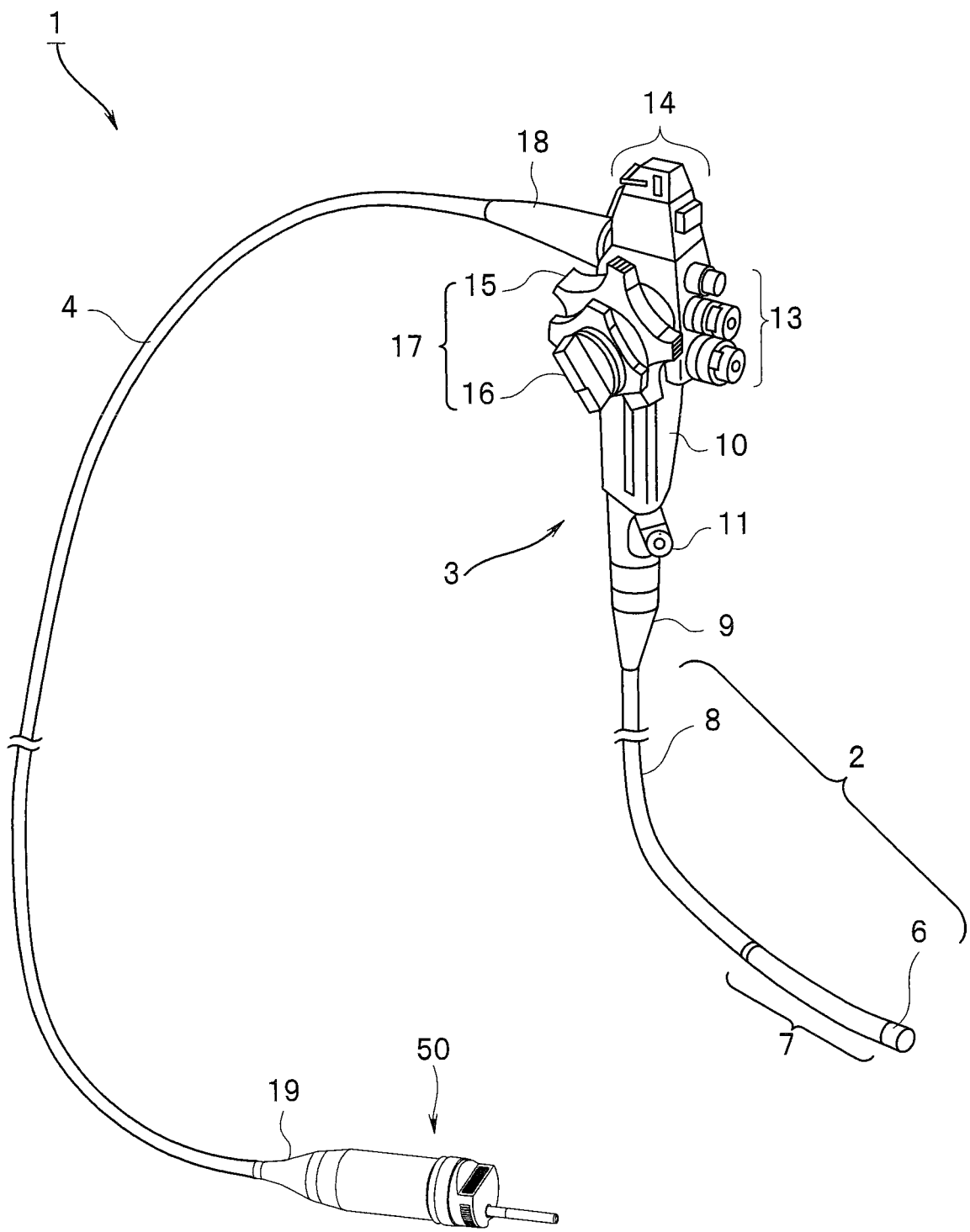
FIG. 3 is a perspective view illustrating an entire configuration of an endoscope apparatus.
Figure 4:
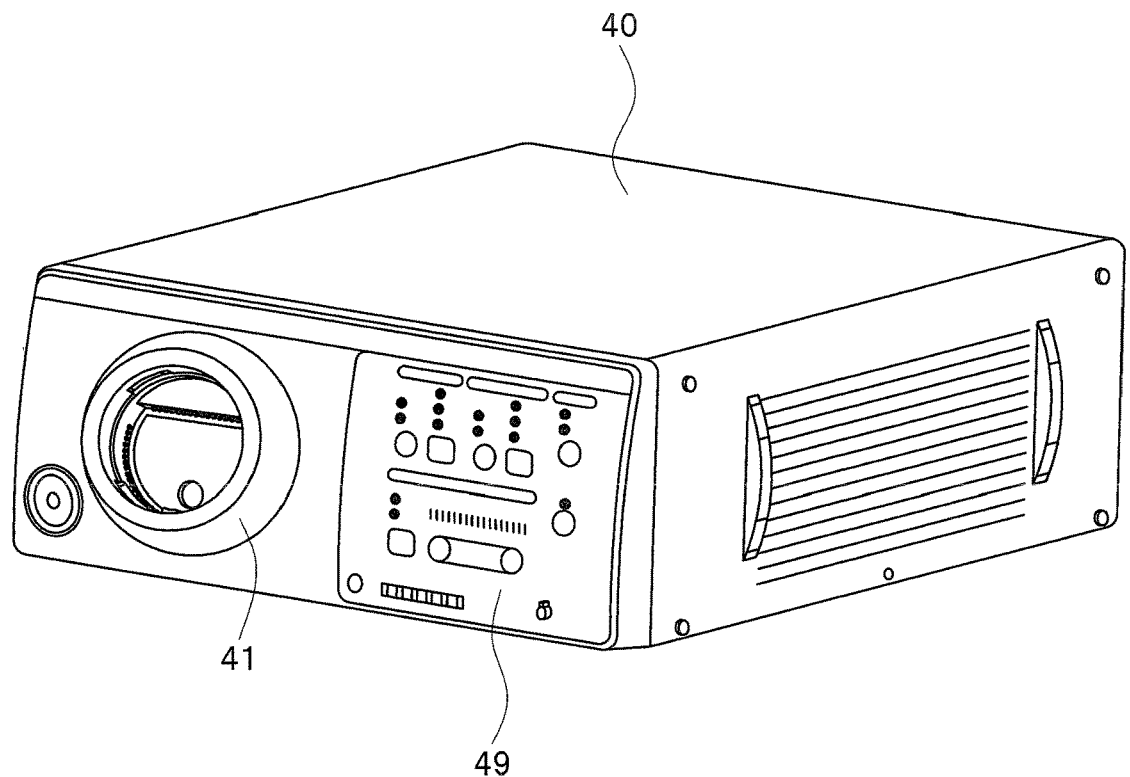
FIG. 4 is a perspective view illustrating an appearance of a processor.
Figure 5:
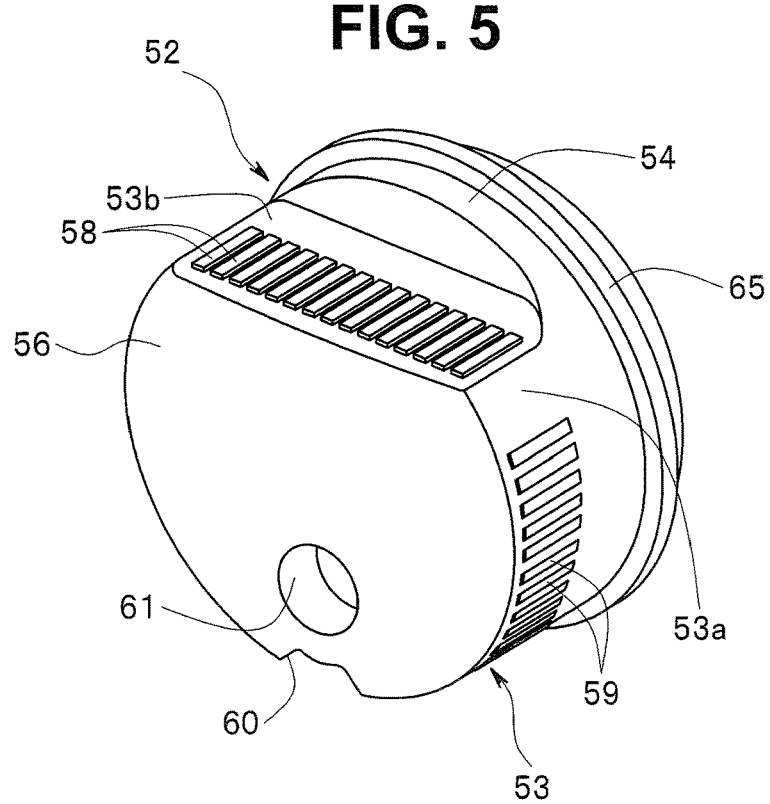
FIG. 5 is a perspective view illustrating the configuration of the endoscope connector.
Figure 6:
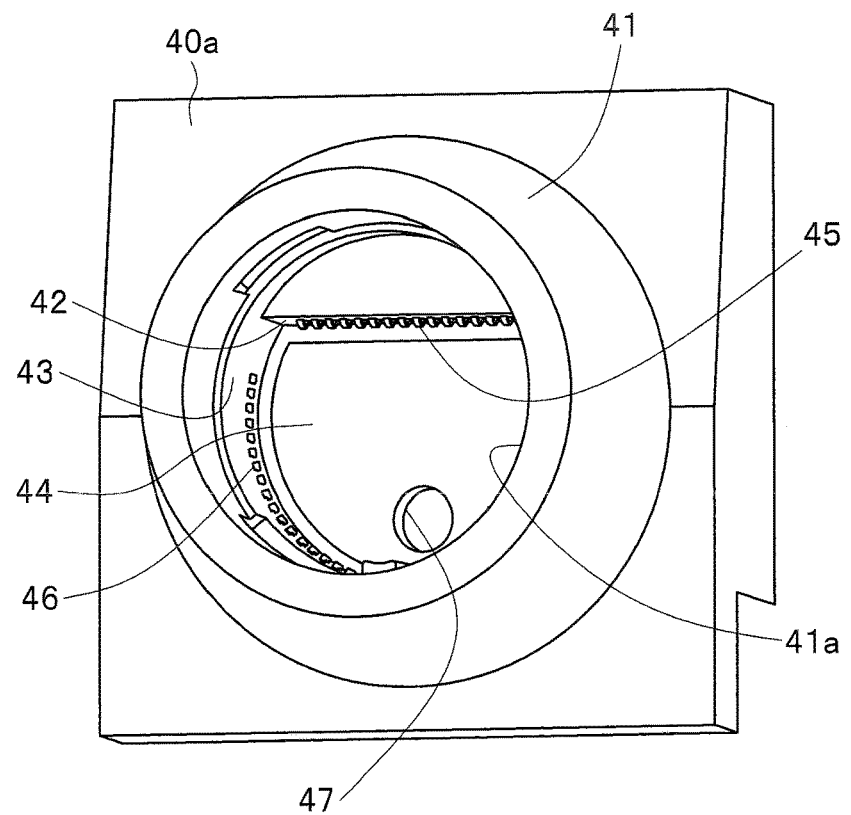
FIG. 6 is a perspective view illustrating a receptacle portion 41 in FIG. 4.
Figure 7:
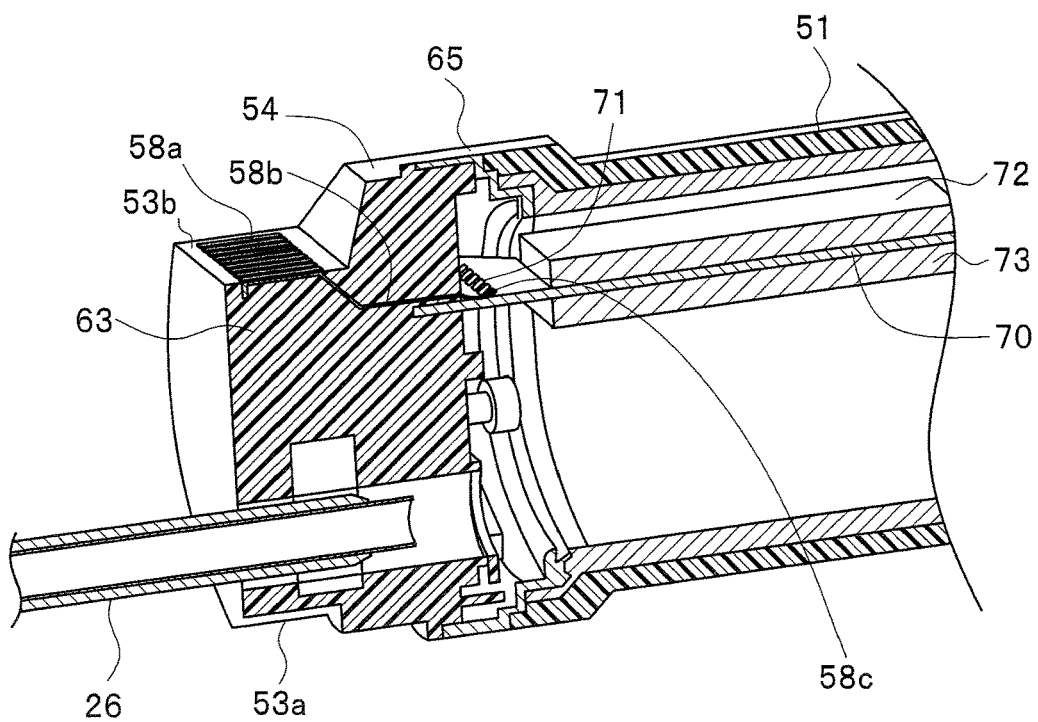
FIG. 7 is a perspective view illustrating a cross-sectional shape of the endoscope connector.
Figure 8:
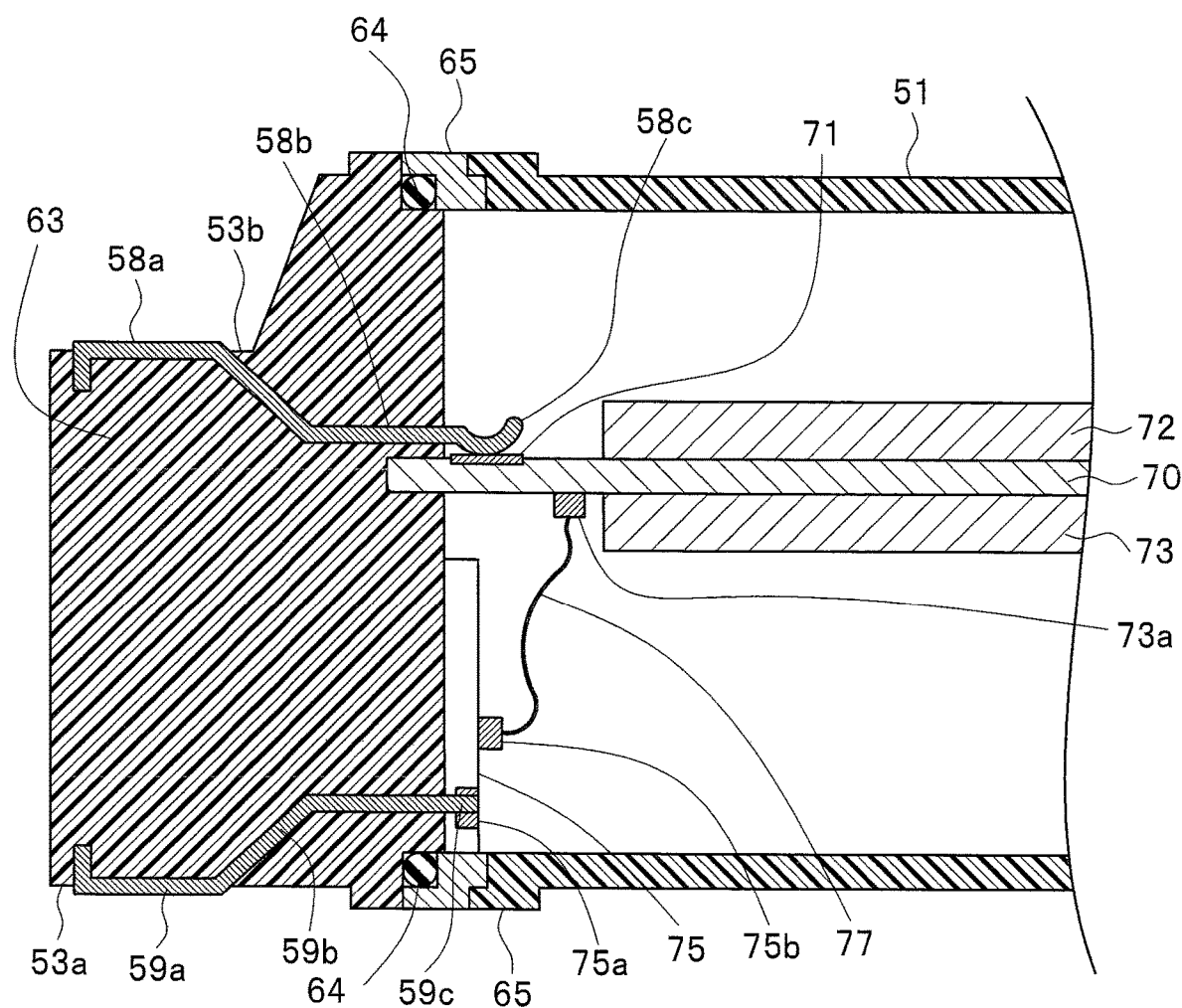
FIG. 8 is a cross-sectional diagram illustrating the configuration of the endoscope connector.

FIG. 1 is a perspective view illustrating an endoscope connector according to a first embodiment of the present invention. FIG. 2 is a perspective view illustrating a configuration of the endoscope connector as viewed from an angle different from an angle of FIG. 1. FIG. 3 is a perspective view illustrating an entire configuration of an endoscope apparatus. FIG. 4 is a perspective view illustrating an appearance of a processor. FIG. 5 is a perspective view illustrating the configuration of the endoscope connector. FIG. 6 is a perspective view illustrating a receptacle portion 41 in FIG. 4. FIG. 7 is a perspective view illustrating a cross-sectional shape of the endoscope connector. FIG. 8 is a cross-sectional diagram illustrating the configuration of the endoscope connector.

Note that, in the following description, drawings based on the respective embodiments are schematic illustrations, relationships between thicknesses and widths of the respective portions, ratios of the thicknesses of the respective portions, and the like are different from actual relationships and actual ratios, and a size and a ratio of a portion may be different between the diagrams in some cases.

As illustrated in FIG. 3, an endoscope apparatus 1 includes an insertion section 2, an operation section 3, a universal cable 4, and an endoscope connector (hereinafter, also simply referred to as a connector) 50. The insertion section 2 serves as an elongated member that is inserted into a lumen of an observation target site such as a large intestine. The operation section 3 is provided continuously with a proximal end portion of the insertion section 2. The universal cable 4 is a composite cable extended from a side surface of the operation section 3. The endoscope connector 50 is provided at an end part of the universal cable 4 and is detachably connected to a light source apparatus and an external apparatus serving as a processor 40. The light source apparatus and the processor, however, may be integrated with each other (see FIG. 4).

The insertion section 2 of the endoscope apparatus 1 includes, on distal end side, a distal end portion 6 in which an image pickup section using a CCD, a CMOS sensor, or the like is installed. A bending portion 7 serving as a bendable movable section is provided continuously with a rear part of the distal end portion 6. Further, an elongated flexible tube portion 8 made of a soft tubular member is provided continuously with a rear part of the bending portion 7. A proximal end part of the flexible tube portion 8 of the insertion section 2 is connected to a bend preventing portion 9 of the operation section 3.

The operation section 3 includes a grasping portion 10 grasped by a user in use. A treatment instrument insertion port 11 that configures a proximal end opening of a treatment instrument channel (not illustrated) disposed inside the insertion section 2, is provided at a connection part between the bend preventing portion 9 and the grasping portion 10. In addition, a bending operation section 17 is provided in the grasping portion 10 of the operation section 3. The bending operation section 17 includes two bending operation knobs 15 and a fixing lever 16. The two bending operation knobs 15 are used to perform bending operation of the bending portion 7 of the insertion section 2. The fixing lever 16 fixes the bending operation knobs 15 at respective desired rotation positions. Further, switches 13 and 14 to operate various kinds of endoscope functions are provided in the grasping portion 10.

The universal cable 4 of the endoscope apparatus 1 includes bend preventing members 18 and 19 at both end parts respectively connected to the operation section 3 and the connector 50. The bend preventing members 18 and 19 respectively cover outer peripheries of the end parts of the universal cable 4 respectively connected to the operation section 3 and the connector 50 to maintain connection strength, thereby preventing damage caused by twist. The connector 50 is attached to the bend preventing member 19 at an end part of the universal cable 4.

In the present embodiment, the connector 50 is connected to the receptacle portion 41 of the processor 40 in FIG. 4. In the following description, the universal cable 4 side of the connector 50 is referred to as proximal end side (or front side), and the side, connected to the processor 40, of the connector 50 is referred to as distal end side (or rear side).

As illustrated in FIG. 1 and FIG. 2, the connector 50 includes a plug section 52 provided on the distal end side, and a connector case 51 provided on the proximal end side. The connector case 51 is a case body formed in a substantially cylindrical shape that has a diameter and a size easily grasped by a hand of an operator, but the diameter of the proximal end side is slightly reduced toward the front side so as to fit an outer shape of the bend preventing member 19.

Electric connection is performed when the plug section 52 of the connector 50 is inserted into the receptacle portion 41 of the processor 40. As described later, the plug section 52 and the receptacle portion 41 are configured such that an outer shape of the plug section 52 is substantially coincident with an inner shape of the receptacle portion 41. Note that a direction of a central axis of a cylindrical shape of the connector case 51 (a central axis of the connector 50) corresponds to an insertion direction of the connector 50 into the receptacle portion 41.

The plug section 52 includes a fitting portion 53 on the distal end side and a connection portion 54 on the proximal end side. The fitting portion 53 is provided with electric contacts (connector contacts) 58 and 59 that configure an electroconductive part. The connection portion 54 is connected to the connector case 51. The fitting portion 53 and the connection portion 54 are integrally configured, and a flange portion 65 is provided on an end part on the distal end side of the connector case 51 and an end part on the proximal end side of the connection portion 54. The flange portion 65 maintains a fitting state with the receptacle portion 41.

In the connection portion 54, the proximal end has an outer peripheral shape substantially same as the outer peripheral shape of the distal end of the connector case 51 in order to facilitate the formation of a watertight structure with the connector case 51. The connection portion 54 and the connector case 51 are fixed to each other. For example, the connection portion 54 and the connector case 51 may be fixed to each other by a screw or the like at an inside predetermined position with an O-shaped ring 64 (see FIG. 8) for water-tightness in between. Further, for example, a distal end of an unillustrated frame housed in the connector case 51 may be attached to the connection portion 54 by a screw or the like. In addition, pressing the connector case 51 against the connection portion 54 through the O-shaped ring 64 by a pressing member such as a screw or the like may water-tightly couple the connector case 51 to the connection portion 54. The pressing member is attached to a proximal end part of the frame that is projected from an opening on the proximal end side of the connector case 51. In the present embodiment, the method of water-tightly coupling the connector case 51 to the connection portion 54 is not particularly limited.

In the present embodiment, the fitting portion 53 has a shape in which a portion of a columnar shape similar to the connection portion 54 is cut out. The fitting portion 53 includes a part having a circumferential surface shape (hereinafter, referred to as a circumferential part) 53a similar to that of the connection portion 54, and a planar portion (hereinafter, referred to as a planar part) 53b parallel to a direction of the central axis of the cylindrical shape of the connector case 51 (hereinafter, simply referred to as a central axis). A rear side end surface of the fitting portion 53 is a plane 56 (hereinafter, a distal end surface) orthogonal to the central axis, and providing the planar part 53b causes the distal end surface 56 to be formed in an arc shape in which a portion of a circle is cut out.

In the present embodiment, the electric contacts (the connector contacts) 59 are provided on the circumferential part 53a of the fitting portion 53, and the electric contacts (the connector contacts) 58 are provided on the planar part 53b. The plurality of connector contacts 59 are provided side by side in a portion of the circumferential surface of the circumferential part 53a. Each of the connector contacts 59 has a predetermined length in the central axis direction of the connector case 51. In addition, the plurality of connector contacts 58 are provided side by side in the longitudinal direction of the planar part 53b on a portion of the surface of the planar part 53b. Each of the connector contacts 58 has a predetermined length in a lateral direction of the planar part 53b that is the central axis direction of the connector case 51.

Note that a cutout 60 that causes the processor 40 to recognize the endoscope apparatus 1 is provided on an edge side of the circumferential part 53a of the fitting portion 53. Moreover, an opening part 61 is provided on the distal end surface 56 of the fitting portion 53 that is the distal end surface of the plug section 52. A light guide 26 is inserted into the opening part 61.

The connector 50 is connected to the receptacle portion 41 provided on a front surface 40a of the processor 40 illustrated in FIG. 6. Inserting the connector 50 into a hole part 41a of the receptacle portion 41 of the processor 40 and fitting the connector 50 to the hole part 41a, which establishes a connection state between the connector 50 and the receptacle portion 41. Note that a panel section 49 for operation of the processor 40 and state display of the processor 40 is provided on the front surface 40a of the processor 40.

The receptacle portion 41 of the processor 40 includes an unillustrated metal attachment part at a predetermined position of the hole part 41a. The flange portion 65 of the connector 50 is fitted and fixed to the attachment part. Note that the metal flange portion 65 and the metal attachment part are fitted and in contact with each other, thereby connecting the ground of the endoscope apparatus 1 to the ground of the processor 40.

Alternatively, it is sufficient for the attachment part to include a metal part for ground connection, or the attachment part may be fitted and fixed by a non-metal member.

A movable shutter that prevents a user from touching to each of receptacle contacts in a non-connection state of the connector 50 may be provided.

The hole part 41a has an inside shape that is substantially coincident with an outer shape of the fitting portion 53 of the connector 50. In other words, the hole part 41a includes a planar part 44, an inner circumferential part 43, and a planar part 42. The planar part 44 is a surface perpendicular to the insertion direction of the connector 50, and has a shape and a size that are substantially same as those of the distal end surface 56 of the fitting portion 53. The inner circumferential part 43 has a shape and a size that are substantially same as those of the circumferential part 53a of the fitting portion 53. The planar part 42 is a planar surface perpendicular to the planar part 44, and has a shape and a size that are substantially same as those of the planar part 53b of the fitting portion 53.

When the fitting portion 53 of the connector 50 is inserted into the hole part 41a, the circumferential part 53a and the planar part 53b of the fitting portion 53 respectively face the inner circumferential part 43 and the planar part 42, and the fitting portion 53 and the hole part 41a are fitted to each other. A plurality of electric contacts (hereinafter, receptacle contacts) 45 are provided on the planar part 42 at respective positions corresponding to the plurality of connector contacts 58 provided on the planar part 53b in the fitting state. A plurality of electric contacts (receptacle contacts) 46 are provided on the inner circumferential part 43 at respective positions corresponding to the plurality of connector contacts 59 provided in the circumferential part 53a in the fitting state. Therefore, the fitting portion 53 of the connector 50 is inserted into the hole part 41a to connect the connector 50 to the receptacle portion 41, which establishes electric connection between the respective connector contacts 58 and the respective receptacle contacts 45 and electric connection between the respective connector contacts 59 and the respective receptacle contacts 46. This makes it possible for the endoscope apparatus 1 and the processor 40 to transmit and receive various kinds of signals.

Note that, in the state in which the connector 50 is connected to the receptacle portion 41, the light guide 26 projected from the opening part 61 of the connector 50 is inserted into an opening part 47 that is provided in the planar part 44. This makes it possible to guide illumination light that has been transmitted from an illumination light source such as a halogen lamp in the processor 40, to the endoscope apparatus 1 through the light guide 26.

Next, electric connection between the connector contacts 58 and 59 of the fitting portion 53 and a circuit substrate 70 is described with reference to FIG. 7 and FIG. 8.

The connector contacts 58 and 59 and the light guide 26 are provided inside the fitting portion 53. Most of the inside of the fitting portion 53 is filled with a resin 63 except for the connector contacts 58 and 59 and a portion into which and the light guide 26 is inserted. The respective positions of the connector contacts 58 and 59 are fixed by the resin 63, and the connector contacts 58 and 59 are insulated from one another by the resin 63.

The circuit substrate 70 is disposed along the central axis and is supported by an unillustrated supporting member, on the connector case 51 side. A concave part is provided at a predetermined position of the resin 63, and the concave part has a counter surface parallel to the planar part 53b and has a width corresponding to the thickness of the circuit substrate 70. The distal end of the circuit substrate 70 is inserted and fitted into the concave part. In other words, the surface of the circuit substrate 70 is parallel to the planar part 53b. Substrate terminals 71 corresponding to the respective connector contacts 58 are provided on the surface on the distal end side of the circuit substrate 70.

A circuit portion 72 configured of a plurality of circuit components is disposed on the surface of the circuit substrate 70 on side on which the substrate terminals 71 are provided. In addition, a circuit portion 73 configured of a plurality of circuit components is disposed on a surface of the circuit substrate 70 on a side opposite to the side on which the substrate terminals 71 are provided. In the present embodiment, the circuit portion 72 is a circuit portion for high-speed transmission suitable for transmission of, for example, a video signal. The circuit portion 73 is a circuit portion for transmission other than the high-speed transmission. The circuit portion for high-speed transmission and the circuit portion for transmission other than the high-speed transmission may be disposed in an arrangement other than the above as long as both circuit portions are disposed on the substrate.

Each of the connector contacts 58 is formed by bending, in a longitudinal direction, a metal elongated plate member that has a constant width, in a predetermined shape. Each of the connector contacts 58 includes a linear contact part 58a, a conductive part 58b, and a contact part 58c. The linear contact part 58a is exposed to the outside on the planar part 53b. The conductive part 58b is bent according to the position of the circuit substrate 70 (the distance between the planar part 53b and the plane of the substrate 70). The contact part 58c is bought into contact with the corresponding substrate terminal 71 of the circuit substrate 70.

In the present embodiment, the respective connector contacts 58 have the same shape, and are disposed parallel to one another with the same interval. Further, the longitudinal direction of each of the connector contacts 58 is coincident with the central axis direction. In the present embodiment, the substrate terminals 71 are arranged in a direction parallel to the arrangement direction of the contact parts 58a on the planar part 53b in a state in which the circuit substrate 70 is inserted and fitted into the resin 63. The interval between the substrate terminals 71 is the same as the interval between the connector contacts 58.

Therefore, in the state in which the circuit substrate 70 is inserted and fitted into the resin 63, the contact part 58c of each of the connector contacts 58 can be configured to be in contact with the corresponding substrate terminal 71. In this case, since the distance between the contact part 58a of each of the connector contacts 58 and the corresponding substrate terminal 71 is the same for all of the connector contacts 58, and the respective connector contacts 58 have the same shape and the same size, impedance between each of the contact part 58a and the corresponding substrate terminal 71 is the same for all of the connector contacts 58.

Accordingly, in the present embodiment, the transmission characteristics by the respective connector contacts 58 are the same as one another. Each of the connector contacts 58 is made of a material excellent in electric characteristics, and is directly connected to the corresponding substrate terminal 71, which eliminates the need for use of other wiring material in connection between the connector contact 58 and the corresponding substrate terminal 71. Therefore, signal transmission through the connector contacts 58 is extremely excellent in transmission characteristics and enables high-speed transmission. For example, in the present embodiment, the connector contacts 58 are used for transmission of a video signal.

The video signal acquired by the image pickup section at the distal end of the insertion section 2 is transmitted to the circuit portion 72 through the insertion section 2, the operation section 3, and the universal cable 4. The circuit portion 72 is mounted on the circuit substrate 70 in the connector case 51 of the connector 50. Connecting the connector 50 to the receptacle portion 41 connects the connector contacts 58 to the receptacle contacts 45, and the circuit portion 72 transmits the video signal from the substrate terminals 71 to a circuit portion of the processor 40 through the connector contacts 58 and the receptacle contacts 45. Since the transmission characteristics between the substrate terminals 71 and the connector contacts 58 are favorable, it is possible for the circuit portion 72 to perform high-speed transmission with the processor 40 serving as the external apparatus, and to transmit a high-resolution video signal and the like without transmission error.

In contrast, the connector contacts 59 are used for the purposes other than the high-speed transmission. For example, the connector contacts 59 may be used for transmission and control of electric power and for information transmission. Each of the connector contacts 59 is formed by bending, in a longitudinal direction, a metal elongated plate member that has a constant width, in a predetermined shape. Each of the connector contacts 59 includes a linear contact part 59a, a conductive part 59b, and a contact part 59c. The linear contact part 59a is exposed to the outside on the circumferential part 53a. The conductive part 59b is bent according to the position of a corresponding terminal 75a of a transmission substrate 75. The contact part 59c is bought into contact with the corresponding terminal 75a of the transmission substrate 75. The substrate 75 includes connectors 75b that are connected to the respective terminals 75a, and the connectors 75b are respectively connected, through a cable 77, to connectors 73a provided in the circuit substrate 70. The electrical conduction between the respective circuits in the circuit portion 73 mounted on the circuit substrate 70 and the respective connector contacts 59 is achieved in such a manner.

Note that, in FIG. 8, an example in which the connector contacts 59 are respectively connected to the connectors 73a of the circuit substrate 70 through the substrate 75 is illustrated; however, the connector contacts 59 may be directly connected to the terminals on the circuit substrate 70. Further, in FIG. 8, the example in which all of the connector contacts 59 are respectively connected to the connectors 73a of the circuit substrate 70 is illustrated; however, a portion or all of the connector contacts 59 may be connected to a circuit portion other than the circuit substrate 70 in the endoscope apparatus 1.

As mentioned above, in the present embodiment, the planar part having the shape in which a portion of the cylindrical shape is cut out in the fitting portion is provided, and the connector contacts are arranged, on the planar part, in the direction perpendicular to the central axis of the connector. Further, the substrate in which the substrate terminals are provided in the direction parallel to the arrangement direction of the connector contacts is disposed in the direction parallel to the central axis, and the distances from the contact parts of the respective connector contacts with the external apparatus to the respective substrate terminals are made equal for all of the connector contacts. This allows for direct connection between the connector contacts and the substrate terminals. In addition, making impedance from the contact parts to the substrate terminals equal for all of the connector contacts improves the transmission characteristics and enables high-speed transmission. Adopting the connector according to the present invention in the above-described manner makes it possible to transmit the high-resolution video signal without transmission error. In addition, in the present embodiment, the connector contacts that are not disposed only by the planar part are disposed with use of the circumferential part of the fitting portion, and using the connector contacts for transmission that does not require high-speed transmission makes it possible to effectively use the circumferential surface of the fitting portion and to dispose sufficient number of connector contacts.

Note that, in the present embodiment, the example of the formation of one planar part having the shape in which a portion of the cylindrical shape of the fitting portion is cut out is illustrated; however, two or more planar parts each having a shape in which a plurality of portions of the cylindrical shape are cut out may be provided. In this case, preparing circuit substrates respectively corresponding to the planar parts allows for high-speed transmission by the circuit substrates.

In addition, to enable high-speed transmission by the circuit substrate, it is sufficient to directly respectively connect the connector contacts to the substrate terminals of the circuit substrate and to make impedance from the contact part of each of the connector contact with the external apparatus to the corresponding substrate terminal equal for all of the connector contacts. Taking the planar circuit substrate into consideration, it is sufficient that the arrangement direction of the respective connector contacts is parallel to the arrangement direction of the substrate terminals. Therefore, the planar portion having the surface parallel to the central axis is described in the above-described embodiment; however, the surface may be slightly inclined from the central axis. Further, since it is sufficient to make the impedance of the respective connector contacts equal to one another, the arrangement of the connector contacts may not be necessarily arranged in parallel to one another or the connector contacts may not be necessarily arranged with equivalent intervals if the wiring pattern is changed.

The invention described in the above-described embodiment is not limited to the embodiment and the modifications, and may be variously modified in implementation without departing from the scope of the invention. Further, the above-described embodiment includes inventions in the various stages, and various inventions may be extracted from appropriate combinations of the plurality of disclosed components.

For example, when the described issues are solved and the described effects are obtained even if some components are removed from all components described in the embodiment, the configuration in which the some components are removed may be extracted as an invention.

The present invention has the effect of enabling direct connection between the connector contacts and the substrate terminals to improve the transmission characteristics by including the planar part at the fitting portion with the receptacle and including the connector contacts disposed on the planar part.

The present invention is not limited to the above-described embodiment, and is variously modified or alternated without departing from the scope of the present invention.

What is claimed is:

1. An endoscope configured to be inserted into an inside of a subject to pick up an image of the inside of the subject, the endoscope comprising:
    a fitting having a cylindrical shape, the fitting being connected to the endoscope, and the fitting being electrically connected to an external apparatus, the external apparatus processing a video signal picked up by the endoscope;
    a light guide provided so as to project from a bottom surface of the cylindrical shape of the fitting, the bottom surface being on a side of the fitting connecting to the external apparatus;
    a planar surface provided on at least a portion of the cylindrical shape of the fitting;
    one or more first electroconductive contacts provided on the planar surface, the one or more electroconductive contacts being configured to communicate with the external apparatus;
    one or more second electroconductive contacts provided on a circumferential surface of the cylindrical shape of the fitting; and
    a planar substrate configured to communicate with the external apparatus, the planar substrate being disposed inside the fitting and arranged along a central axis of the cylindrical shape, the planar substrate being disposed parallel to the planar surface,
    wherein the one or more second electroconductive contacts are electrically connected to the substrate via a cable, the one or more second electroconductive contacts being configured for transmission and control of electric power and for information transmission,
    the one or more first electroconductive contacts are directly electrically connected to the planar substrate, the one or more first electroconductive contacts being configured for transmission of the video signal; and
    the one or more first electroconductive contacts are configured for transmission of the video signal at a transmission speed higher than a transmission speed of information transmitted by the one or more second electroconductive contacts.

2. The endoscope according to claim 1, wherein
    the one or more first electroconductive contacts comprises a plurality of first electroconductive contacts each electrically conductive with the external apparatus,
    the plurality of first electroconductive contacts are respectively electrically connected to a plurality of substrate terminals disposed on the planar substrate, and
    an impedance from the plurality of first electroconductive contacts to each of the respective plurality of substrate terminals is equal.

3. The endoscope according to claim 2, wherein
    the plurality of first electroconductive contacts have a same shape as one another, and
    the plurality of first electroconductive contacts are respectively connected to the plurality of substrate terminals at equal distances.

4. The endoscope according to claim 2, wherein the plurality of first electroconductive contacts are arranged in a direction parallel to an arrangement direction of the plurality of substrate terminals.

5. The endoscope according to claim 1, wherein the fitting includes a cutout provided in a region of the circumferential surface of the cylindrical shape of the fitting that is not provided with the one or more second electroconductive contacts.

6. The endoscope according to claim 1, wherein the bottom surface is orthogonal to the central axis of the cylindrical shape, the fitting having an opening into which the light guide is inserted, the opening being provided on the bottom surface.

7. The endoscope according to claim 1, wherein
    the one or more first electroconductive contacts comprises three or more first electroconductive contacts arranged on the planar surface,
    the three or more first electroconductive contacts each having a same shape, and
    the three or more first electroconductive contacts each comprising a first portion exposed on the planar surface, a second portion disposed at a proximal end of the first portion, the second portion being connected to a respective substrate terminal arranged on the planar substrate, and a third portion electrically connecting the first and second portions to each other.

* * * * *